United States Patent
Sonobe et al.

(10) Patent No.: US 10,441,551 B2
(45) Date of Patent: Oct. 15, 2019

(54) PATCH

(71) Applicant: HISAMITSU PHARMACEUTICAL CO., INC., Tosu-shi, Saga (JP)

(72) Inventors: Atsushi Sonobe, Tsukuba (JP); Akio Takeuchi, Tosu (JP); Yasunori Takada, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 0 days.

(21) Appl. No.: 15/769,393

(22) PCT Filed: Oct. 24, 2016

(86) PCT No.: PCT/JP2016/081446
§ 371 (c)(1),
(2) Date: Apr. 19, 2018

(87) PCT Pub. No.: WO2017/073516
PCT Pub. Date: May 4, 2017

(65) Prior Publication Data
US 2018/0289630 A1 Oct. 11, 2018

(30) Foreign Application Priority Data
Oct. 26, 2015 (JP) .................. 2015-209736

(51) Int. Cl.

| | |
|---|---|
| *A61K 9/70* | (2006.01) |
| *A61K 47/02* | (2006.01) |
| *A61K 47/10* | (2017.01) |
| *A61K 47/14* | (2017.01) |
| *A61K 47/20* | (2006.01) |
| *A61K 47/22* | (2006.01) |
| *A61K 47/32* | (2006.01) |
| *A61K 47/44* | (2017.01) |
| *A61K 31/4468* | (2006.01) |

(52) U.S. Cl.
CPC .............. *A61K 9/7053* (2013.01); *A61K 9/70* (2013.01); *A61K 9/7069* (2013.01); *A61K 31/4468* (2013.01); *A61K 47/02* (2013.01); *A61K 47/10* (2013.01); *A61K 47/14* (2013.01); *A61K 47/20* (2013.01); *A61K 47/22* (2013.01); *A61K 47/32* (2013.01); *A61K 47/44* (2013.01)

(58) Field of Classification Search
None
See application file for complete search history.

(56) References Cited

U.S. PATENT DOCUMENTS

| 6,132,761 | A | 10/2000 | Muraoka et al. | |
|---|---|---|---|---|
| 2003/0124176 | A1* | 7/2003 | Hsu | A61K 8/0208 424/449 |
| 2003/0170295 | A1* | 9/2003 | Kim | A61K 9/7053 424/449 |
| 2003/0212083 | A1* | 11/2003 | Riebesehl | A61K 45/06 514/265.1 |
| 2008/0131490 | A1 | 6/2008 | Hanatani et al. | |
| 2012/0226245 | A1 | 9/2012 | Kawamura et al. | |
| 2012/0251610 | A1 | 10/2012 | Enomoto et al. | |

FOREIGN PATENT DOCUMENTS

| JP | 10-45570 A | 2/1998 |
|---|---|---|
| JP | 11-79979 A | 3/1999 |
| JP | 2010-6761 A | 1/2010 |
| JP | 2010-6762 A | 1/2010 |
| JP | 2010-30909 A | 2/2010 |
| JP | 2012-214425 A | 11/2012 |
| WO | 2008/066180 A1 | 6/2008 |
| WO | 2009/157586 A1 | 12/2009 |
| WO | 2011/027786 A1 | 3/2011 |
| WO | 2011/118604 A | 9/2011 |
| WO | 2015/177209 A1 | 11/2015 |
| WO | 2015/177212 A1 | 11/2015 |
| WO | 2016/052522 A1 | 4/2016 |

OTHER PUBLICATIONS

Machine Translation of JP 2010-006761 (Year: 2010).*
International Preliminary Report on Patentability dated May 11, 2018 in International Application No. PCT/JP2016/0181446.
International Search Report for PCT/JP2016/081446, dated Dec. 6, 2016 (PCT/ISA/210).

* cited by examiner

*Primary Examiner* — Jennifer A Berrios
(74) *Attorney, Agent, or Firm* — Sughrue Mion, PLLC

(57) ABSTRACT

A patch comprises a backing and an adhesive layer laminated on at least one surface of the backing, in which the adhesive layer contains at least one selected from the group consisting of fentanyl and salts thereof, and contains an adhesive base material and an antioxidant having a sulfur atom in its molecule.

10 Claims, No Drawings

PATCH

CROSS REFERENCE TO RELATED APPLICATIONS

This application is a National Stage of International Application No. PCT/JP2016/081446 filed Oct. 24, 2016, claiming priority based on Japanese Patent Application No. 2015-209736, filed Oct. 26, 2015.

TECHNICAL FIELD

The present invention relates to a patch, and more specifically to a patch comprising a backing and an adhesive layer, wherein the adhesive layer contains, as a drug, at least one selected from the group consisting of fentanyl (chemical name: N-(1-phenethylpiperidin-4-yl)-N-phenylpropionamide) and salts thereof.

BACKGROUND ART

Heretofore, injections containing fentanyl or a salt thereof as a drug have been used as analgesic agents for cancer pain and the like. In recent years, in addition to the injections, patches containing fentanyl or a salt thereof have been developed, and have been studied on matters such as improvements in transdermal absorbability and temporal stability of the drug.

For example, Japanese Unexamined Patent Application Publication No. Hei 10-45570 (PLT 1) discloses a fentanyl-containing transdermal administration tape preparation containing fentanyl or a salt thereof, an adhesive, and sodium acetate, and states that antioxidants which may be added to the preparation as optional ingredients antioxidant include tocopherol and ester derivatives thereof, ascorbic acid, stearic acid ester, nordihydroguaiaretic acid, dibutylhydroxytoluene (BHT), butylhydroxyanisole (BHA), and the like.

In addition, Japanese Unexamined Patent Application Publication No. 2010-30909 (PLT 2) discloses a transdermal absorption patch in which an adhesive layer contains an effective amount of fentanyl or a salt thereof, and a sufficient amount of a hindered phenolic antioxidant to inhibit precipitation of the fentanyl or the salt thereof, and mentions, as the hindered phenolic antioxidant, 2,6-di-t-butyl-p-cresol, pentaerythrityl tetrakis [3-(3,5-di-t-butyl-4-hydroxyphenyl) propionate], and the like.

Furthermore, Japanese Unexamined Patent Application Publication No. 2010-6761 (PLT 3) discloses a transdermal absorption patch containing fentanyl or a salt thereof and containing a rosin resin treated with an antioxidant, and states that one kind or a combination of two or more kinds among tocopherol and ester derivatives thereof, ascorbic acid, ascorbic acid esters, nordihydroguaiaretic acid, and phenolic antioxidants is used as the antioxidant.

In addition, Japanese Unexamined Patent Application Publication No. 2010-6762 (PLT 4) discloses a pharmaceutical composition containing fentanyl or a salt thereof and containing 0.01 to 0.5% by mass of ascorbic acid or an ester thereof, and states that the pharmaceutical composition may further contain a phenolic antioxidant, tocopherol or an ester derivative thereof, nordihydroguaiaretic acid, butylhydroxyanisole, or the like as an antioxidant other than the ascorbic acid or the ester thereof.

CITATION LIST

Patent Literature

[PTL 1] Japanese Unexamined Patent Application Publication No. Hei 10-45570
[PTL 2] Japanese Unexamined Patent Application Publication No. 2010-30909
[PTL 3] Japanese Unexamined Patent Application Publication No. 2010-6761
[PTL 4] Japanese Unexamined Patent Application Publication No. 2010-6762

SUMMARY OF INVENTION

Technical Problem

Despite of these disclosures, patches containing fentanyl or a salt thereof are still required to achieve more advanced performance in these days. The present inventors have found that obtaining a patch is extremely useful if the obtained patch is excellent in basic performance such as transdermal absorbability of a drug, and additionally is superior to a conventional patch in terms of temporal stability of the drug owing to an ability to more reliably prevent the drug from degrading over time.

The present invention was made in view of the above problems, and has an object to provide a clinically useful transdermal administration patch that is a patch comprising at least one selected from the group consisting of fentanyl and salts thereof as a drug, and is notably improved in temporal stability of the drug as compared with a conventional patch without deteriorating basic performance such as transdermal absorbability of the drug.

Solution to Problem

The present inventors have intensively studied to achieve the above object, and resultantly have found that a patch comprising an adhesive layer containing at least one selected from the group consisting of fentanyl and salts thereof, and an adhesive base material is made capable of more reliably preventing the drug from degrading over time without deteriorating the basic performance such as the transdermal absorbability of the drug, when the adhesive layer contains, as an antioxidant, an antioxidant having a sulfur atom in its molecule, thereby completing the present invention.

A patch of the present invention comprises a backing and an adhesive layer laminated onto at least one surface of the backing, wherein the adhesive layer contains at least one selected from the group consisting of fentanyl and salts thereof, and contains an adhesive base material and an antioxidant having a sulfur atom in its molecule.

In the patch of the present invention, the antioxidant having a sulfur atom in its molecule is preferably at least one selected from the group consisting of 2-mercaptobenzimidazole and sodium metabisulfite.

In addition, in the patch of the present invention, the adhesive base material is preferably a rubber-based adhesive base material.

Moreover, in the patch of the present invention, it is preferable that a content of the fentanyl and the salts thereof be 0.05 to 20% by mass relative to a total mass of the adhesive layer, a content of the adhesive base material be 0.1 to 98% relative to the total mass of the adhesive layer in terms of solid content, and a content of the antioxidant having a sulfur atom in its molecule be 0.01 to 5% by mass relative to the total mass of the adhesive layer.

Further, in the patch of the present invention, the adhesive layer preferably further contains a fatty acid ester as an absorption enhancer, and in this case, a content of the absorption enhancer is preferably 0.01 to 20% by mass relative to the total mass of the adhesive layer.

Still further, in the patch of the present invention, the adhesive layer preferably further contains a phenolic antioxidant, and in this case, a content of the phenolic antioxidant is preferably 0.01 to 5% by mass relative to the total mass of the adhesive layer.

Furthermore, in the patch of the present invention, the adhesive layer preferably further contains, as a desalting agent, at least one selected from the group consisting of basic alkaline (earth) metal salts, alkali (earth) metal hydroxides, and low-molecular weight compounds containing basic nitrogen, and in this case, a content of the desalting agent is preferably 0.01 to 15% by mass relative to the total mass of the adhesive layer.

Still further, in the patch of the present invention, the adhesive layer preferably further contains, as a tackifier, at least one selected from the group consisting of alicyclic saturated hydrocarbon resins, terpene resins, rosin resins, rosin ester resins, and oil-soluble phenolic resins, and in this case, a content of the tackifier is preferably 0.1 to 70% by mass relative to the total mass of the adhesive layer.

Additionally, in the patch of the present invention, the adhesive layer preferably further contains, as a softener, at least one selected from the group consisting of liquid paraffin, squalane, olive oil, camellia oil, persic oil, and arachis oil, and in this case, a content of the softener is preferably 1 to 70% by mass relative to the total mass of the adhesive layer.

Advantageous Effects of Invention

According to the present invention, a patch containing as a drug at least one selected from the group consisting of fentanyl and salts thereof can be made capable of more reliably preventing the drug from degrading over time without deteriorating the basic performance such as the transdermal absorbability of the drug, so that it is possible to provide a clinically useful transdermal administration patch that is notably superior to a conventional patch in terms of the temporal stability of the drug.

DESCRIPTION OF EMBODIMENTS

Hereinafter, the present invention is described in detail using its preferred embodiments.

A patch of the present invention is a patch comprising a backing and an adhesive layer laminated on at least one surface of the backing, in which the adhesive layer contains at least one selected from the group consisting of fentanyl and salts thereof, and contains an adhesive base material and an antioxidant having a sulfur atom in its molecule.

The backing may be any backing generally used for patches, and materials preferably usable for the backing include, but not limited to, polyesters such as polyethylene terephthalate (PET), polybutylene terephthalate, and polyethylene naphthalate; polyolefin such as polyethylene and polypropylene; nylon; polycarbonate; and metals such as aluminum. The backing is preferably used in a form such as a film form, a fabric form, a foil form, and a porous sheet form, or in a laminate form of them.

In the patch of the present invention, the adhesive layer is laminated on at least one surface of the backing. Then, in the patch of the present invention, at least one selected from the group consisting of fentanyl and salts thereof, an adhesive base material, and an antioxidant having a sulfur atom in its molecule are contained in the adhesive layer.

A pharmacologically active substance (drug) in the patch of the present invention is at least one selected from the group consisting of fentanyl per se and salts thereof. The fentanyl salts are not particularly limited as long as they are pharmaceutically acceptable salts, may be inorganic salts or organic salts, and may be typical fentanyl salts such as citrate, hydrochloride, and fumarate. Among them, the fentanyl citrate is particularly preferable. Note that the fentanyl or the salts thereof may be used singly or in combination of two or more of them.

Then, the content of the fentanyl and the salts thereof is preferably 0.05 to 20% by mass relative to the total mass of the adhesive layer in the patch of the present invention. If the content of the fentanyl and the salts thereof is less than 0.05% by mass, the obtained patch tends to have a difficulty in causing a sufficient amount of the drug to permeate, whereas if the content exceeds 20% by mass, the physical properties per se of the preparation per se of the obtained patch tend to be subject to likely adverse effects.

The adhesive base material contained in the adhesive layer in the patch of the present invention is preferably a hydrophobic adhesive base material, which may be a rubber-based adhesive base material or an acrylic adhesive base material. The rubber-based adhesive base material is more preferable. In the case of the patch of the present invention using a rubber-based adhesive base material as the adhesive base material, the skin permeation rate of the drug is higher than in the case where an acrylic adhesive base material is used, and accordingly the transdermal absorbability of the drug tends to improve. Preferable examples of the rubber-based adhesive base material include, but not particularly limited to, polyisobutylene (PIB) [for example, Oppanol B12, B15, B50, B80, B100, B120, B150, and B220 manufactured by BASF SE, and so on), styrene-isoprene-styrene block copolymers (SIS) [for example, Cariflex D-1111 and Cariflex TR-1107 manufactured by Shell Chemicals Japan Ltd.; JSR5000, JSR-5002, and SR5100 manufactured by JSR Corporation; Quintac 3421 manufactured by Zeon Corporation; and so on], isoprene rubber, styrene-butadiene-styrene block copolymers (SBS) [for example, Cariflex TR-1101 manufactured by Shell Chemicals Japan Ltd., and so on], and the like. Meanwhile, preferable examples of the acrylic adhesive base material include, but not particularly limited to, copolymers of two or more monomers selected from monomers such as 2-ethylhexyl acrylate, vinyl acetate, ethyl acrylate, methacrylate, methoxyethylacrylate, and acrylic acid [for example, PE-300 manufactured by NIPPON CARBIDE INDUSTRIES CO., INC.; Duro-Tak87-4287, Duro-Tak87-4098, and Duro-Tak 87-2194 manufactured by Henkel AG & Co. KGaA; and so on], and the like. One of these adhesive base materials may be used singly, or two or more of them may be used in mixture. In the present invention, it is particularly preferable to use a combination of PIB and SIS as the adhesive base material from the viewpoints that the transdermal absorbability and the temporal stability of the drug tend to improve more, and the adhesive force to the skin tends to improve.

Then, the content of the adhesive base material relative to the total mass of the adhesive layer in the patch of the present invention (in terms of solid content for the adhesive base material) is preferably 0.1 to 98% by mass, more preferably 0.1 to 70% by mass, and particularly preferably 0.1 to 50% by mass. If the content of the adhesive base material is less than the lower limit, the physical properties of the patch preparation per se of the obtained patch tend to be subject to likely adverse effects, whereas if the content exceeds the upper limit, it tends to be difficult to obtain the favorable adhesive force to the skin.

In the patch of the present invention, the adhesive layer containing the at least one selected from the group consisting of fentanyl and salts thereof and the adhesive base material further contains, as the antioxidant, the antioxidant having a sulfur atom in its molecule. The use of the antioxidant having a sulfur atom in its molecule enables the patch to more reliably prevent the drug from degrading over time without deteriorating the basic performance such as the transdermal absorbability of the drug.

As the antioxidant having a sulfur atom in its molecule include from the viewpoint that the effect of inhibiting drug degradation tends to become higher, preferable examples of, but not particularly limited to, imidazole antioxidants (such as 2-mercaptobenzimidazole (2-MBI)), sodium metabisulfite, sodium thioglycolate, N-acetylcysteine, thioglycerol, and the like. Note that one of these antioxidants having a sulfur atom in its molecule may be used singly, or two or more of them may be used in mixture. Further, in the present invention, from the viewpoint that the effect of inhibiting drug degradation tends to become particularly high, it is particularly preferable to use, as the antioxidant having a sulfur atom in its molecule, at least one selected from the group consisting of 2-mercaptobenzimidazole and sodium metabisulfite.

Moreover, the content of antioxidant having a sulfur atom in its molecule relative to the total mass of the adhesive layer in the patch of the present invention is preferably 0.01 to 5% by mass and more preferably 0.1 to 3% by mass. If the content of the antioxidant having a sulfur atom in its molecule is less than the lower limit, it tends to be difficult to sufficiently prevent the drug from degrading over time, whereas if the content exceeds the upper limit, the addition effect on the drug degradation inhibition tends to become smaller.

In the patch of the present invention, the adhesive layer preferably further contains a phenolic antioxidant as an antioxidant in addition to the antioxidant having a sulfur atom in its molecule. When the phenolic antioxidant is further contained, the stability of the physical properties of the preparation tends to improve more. Preferable examples of the phenolic antioxidant include, but not particularly limited to, hindered phenolic antioxidants such as dibutylhydroxytoluene (BHT) and butylhydroxyanisole (BHA). Note that one of these phenolic antioxidants may be used singly, or two or more of them may be used in mixture. Then, in the case where the phenolic antioxidant is contained, the content of the phenolic antioxidant relative to the total mass of the adhesive layer in the patch of the present invention is preferably 0.01 to 5% by mass and more preferably 0.1 to 3% by mass.

In the patch of the present invention, the adhesive layer may further contain other additives to be described below in addition to the at least one selected from the group consisting of fentanyl and salts thereof, the adhesive base material, and the antioxidant having a sulfur atom in its molecule mentioned above, the other additives including a desalting agent (base), a tackifier, a softener (plasticizer), an absorption enhancer, a hydrophilic polymer, a crosslinking agent, a preservative, a filler, and the like. Among them, it is preferable to contain at least one selected from the group consisting of desalting agents (bases), tackifiers, softeners, and absorption enhancers.

When the adhesive layer in the patch of the present invention contains a desalting agent (base), the skin permeability of the at least one selected from the group consisting of fentanyl and salts thereof (in particular, a fentanyl salt) tends to improve more. The desalting agent (base) is not particularly limited, but may be a basic alkaline (earth) metal salt, an alkali (earth) metal hydroxide, a low-molecular weight compound containing basic nitrogen, or the like. More specific examples include sodium hydroxide, potassium hydroxide, magnesium hydroxide, sodium carbonate, potassium carbonate, sodium hydrogencarbonate, potassium hydrogencarbonate, sodium borate, sodium silicate, sodium citrate, sodium acetate, potassium acetate, triethanolamine, diethanolamine, diisopropanolamine, and the like.

The content of the desalting agent (base) relative to the total mass of the adhesive layer is preferably 0.01 to 15% by mass, more preferably 0.01 to 10% by mass, and particularly preferably 0.01 to 5% by mass. If the content of the desalting agent (base) is less than the lower limit, it tends to be difficult to obtain the effect of improving the skin permeability, whereas if the content exceeds the upper limit, the adhesiveness to the skin tends to decrease.

In the patch of the present invention, the adhesive layer may contain a tackifier for the purpose of enhancing the tackiness. Preferable examples of the tackifier include, but not particularly limited to, alicyclic saturated hydrocarbon resins (petroleum resins) [for example, ARKON P-100 manufactured by Arakawa Chemical Industries, Ltd., and so on], terpene resins [for example, Clearon P-105 and YS resin 75 manufactured by YASUHARA CHEMICAL CO., LTD., and so on], rosin resins [for example, KR-610 manufactured by Arakawa Chemical Industries, Ltd., and so on], rosin ester resins [for example, Foral 105 manufactured by Rika Hercules Inc.; KE-311, KE-100 and Super Ester S-100 manufactured by Arakawa Chemical Industries, Ltd.; and so on], oil-soluble phenolic resins [for example, TAMANOL 521 manufactured by Arakawa Chemical Industries, Ltd., and so on], and the like.

The content of the tackifier relative to the total mass of the adhesive layer in the patch of the present invention is preferably 0.1 to 70% by mass, more preferably 5 to 50% by mass, and particularly preferably 10 to 45% by mass. If the content of the tackifier is less than the lower limit, it tends to be difficult to obtain the sufficient effect of improving the tackiness, whereas if the content exceeds the upper limit, the adhesive force becomes so high that the patch tends to cause skin irritation more likely.

In the patch of the present invention, the adhesive layer may contain a softener (plasticizer) for the purposes of improving the processability and adjusting the tackiness. Preferable examples of the softener (plasticizer) include, but not particularly limited to, fats and oils, and more specifically, liquid paraffin, squalane, olive oil, camellia oil, persic oil, arachis oil, and so on. Among them, the liquid paraffin is particularly preferable.

The content of the softener relative to the total mass of the adhesive layer in the patch of the present invention is preferably 1 to 70% by mass, more preferably 10 to 60% by mass, and particularly preferably 20 to 50% by mass. If the content of the softener is less than the lower limit, it tends to be difficult to obtain the addition effects such as processability improvement and tackiness adjustment, whereas if the content exceeds the upper limit, the cohesive force of the adhesive tends to decrease.

In the patch of the present invention, the adhesive layer may also contain an absorption enhancer for the purpose of enhancing the transdermal absorption of at least one selected from the group consisting of fentanyl and salts thereof. The absorption enhancer may be any compound recognized as producing an action of enhancing the absorption through the skin, and preferable examples thereof include, but not particularly limited to, fatty acids, fatty alcohols, fatty acid esters, fatty acid ethers, aromatic organic acids, aromatic alcohols, aromatic organic acid esters, aromatic organic acid ethers, and so on. It is preferable that these compounds have 6 to 20 carbon chains. In addition, as the absorption enhancer, there are lactic acid esters, acetate esters, monoterpene compounds, sesquiterpene compounds, azone, azone derivatives, glycerin fatty acid esters, propylene glycol fatty acid esters, sorbitan fatty acid esters, polysorbates, polyethylene glycol fatty acid esters, polyoxyethylene hydrogenated castor oils, sucrose fatty acid esters, and so on. As such absorption enhancers, specifically there are caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methyl laurate, lauric acid diethanolamide, isopropyl myristate, myristyl myristate, octyl dodecyl myristate, cetyl palmitate, isopropyl palmitate, diethyl sebacate, salicylic acid, methyl salicylate, ethylene glycol salicylate, cinnamic acid, methyl cinnamate, cresol, cetyl lactate, ethyl acetate, propyl acetate, geraniol, thymol, eugenol, terpineol, 1-menthol, borneol, d-limonene, isoeugenol, isoborneol, nerol, dl-camphor, glycerol monolaurate, glycerol monooleate, sorbitan monolaurate, sucrose monolaurate, propylene glycol, propylene glycol monolaurate, propylene glycol monostearate, propylene glycol monooleate, polysorbate 20, polyethylene glycol monolaurate, polyethylene glycol monostearate, HCO-60 (hydrogenated castor oil), and so on. Among these absorption enhancers, a fatty acid ester is preferable, a propylene glycol fatty acid ester is more preferable, and propylene glycol monolaurate, propylene glycol monostearate, and propylene glycol monooleate are particularly preferable from the viewpoint that the effect of enhancing the transdermal absorption of the drug tends to become higher. In addition, in the case where a propylene glycol fatty acid ester is used as an absorption enhancer, the adhesive layer tends to more reliably prevent the occurrence of so-called bleeding (the bleeding of a liquid ingredient to the surface of the adhesive layer).

The content of the absorption enhancer relative to the total mass of the adhesive layer in the patch of the present invention is preferably 0.01 to 20% by mass, more preferably 0.1 to 10% by mass, and particularly preferably 0.5 to 5% by mass. If the content of the absorption enhancer is less than the lower limit, it tends to be difficult to obtain the addition effect of the absorption enhancer, whereas if the content exceeds the upper limit, the skin irritating properties which may cause rubefaction, edema, and so on tend to become stronger.

In the patch of the present invention, the adhesive layer may also contain a hydrophilic polymer for the purpose of absorbing a watery component, such as sweat, generated from the skin. Preferable examples of the hydrophilic polymer include, but not particularly limited to, light anhydrous silicic acid, cellulose derivatives (for example, carboxymethyl cellulose (CMC), sodium carboxymethyl cellulose (CMCNa), methyl cellulose (MC), hydroxypropyl methyl cellulose (HPMC), hydroxypropyl cellulose (HPC), and hydroxyethyl cellulose (HEC)), starch derivatives (pullulan), polyvinyl alcohol (PVA), polyvinylpyrrolidone (PVP), vinyl acetate (VA), carboxyvinyl polymer (CVP), ethyl vinyl acetate (EVA), Eudragit, gelatin, polyacrylic acid, polyacrylic acid soda, polyisobutylene maleic anhydride copolymer, alginic acid, sodium alginate, carrageenan, gum arabic, tragacanth, gumkaraya, polyvinyl methacrylate, and so on. Among them, light anhydrous silicic acid, cellulose derivatives (CMCNa, HPMC, HPC, and MC), and Eudragit are preferable.

The content of the hydrophilic polymer relative to the total mass of the adhesive layer in the patch of the present invention is preferably 0.1 to 20% by mass and more preferably 0.5 to 10% by mass. If the content of the hydrophilic polymer is less than the lower limit, it tends to be difficult to obtain the addition effect of the hydrophilic polymer, whereas if the content exceeds the upper limit, the transdermal absorbability of the drug tends to decrease.

In the patch of the present invention, it is also possible to blend other additive ingredients such as crosslinking agents, preservatives, and fillers as needed. Preferable examples of the crosslinking agents include, but not particularly limited to: thermosetting resins such as amino resin, phenol resin, epoxy resin, alkyd resin, and unsaturated polyester; isocyanate compounds; blocked isocyanate compounds; organic crosslinking agents; inorganic crosslinking agents such as metal or metal compounds; and so on. Meanwhile, preferable examples of the preservatives include, but not particularly limited to, ethyl parahydroxybenzoate, propylparahydroxybenzoate, butylparahydroxybenzoate, and so on. Preferable examples of the fillers include, but not particularly limited to, calcium carbonate, magnesium carbonate, silicates (aluminum silicate, calcium silicate, magnesium silicate, and so on), and cellulose derivatives (hydroxypropylcellulose, hydroxypropylmethylcellulose, carboxymethylcellulose, and so on).

Note that the thickness of the adhesive layer in the patch of the present invention is not particularly limited, but is preferably 30 to 500 µm and more preferably 40 to 300 µm in general.

In addition, in the patch of the present invention, the surface of the adhesive layer on the opposite side to the backing may be covered with a release liner. This release liner is a release film for covering and protecting the adhesive layer, and is not particularly limited but may be any release liner generally used for patches. Examples of materials for such release liners include: resin films made of polyester (such as polyethylene terephthalate, polyethylene naphthalate, and polybutylene terephthalate), polyolefin (such as polyethylene and polypropylene), and the like; paper; cellulose derivatives; and the like. A preferable release liner is one in which the surface to be in contact with the adhesive layer is coated by release treatment with silicone, Teflon (registered trademark), or the like, and it is preferable to use a silicone-treated polyethylene terephthalate film in particular.

A method for producing the patch of the present invention is not particularly limited. The patch of the present invention can be obtained by a general patch production method (a solvent method, a hot melt method, or the like). In the case of production by a solvent method, for example, the patch of the present invention can be obtained by: mixing, in an organic solvent, the aforementioned adhesive base material, at least one selected from the group consisting of fentanyl and salts thereof, antioxidant having a sulfur atom in its molecule, and other additive ingredients as needed; applying the obtained adhesive solution to a release liner; removing the solvent by drying; laminating a backing onto the formed adhesive layer; and then cutting the obtained patch sheet in an appropriate size. Alternatively, in the case where the adhesive base material to be contained can be applied by a hot melt method, the patch of the present invention can be obtained by: after melting the adhesive base material at high temperature, adding the at least one selected from the group consisting of fentanyl and salts thereof, the antioxidant having a sulfur atom in its molecule, and other additive ingredients as needed to the melted adhesive base material, followed by mixing; applying the obtained adhesive solution to a release liner, followed by cooling; laminating a backing onto the formed adhesive layer; and then cutting the obtained patch sheet in an appropriate size.

EXAMPLES

Hereinafter, the present invention is described in more details based on Examples and Comparative Examples. It should be noted that the present invention is not limited to Examples described below.

Examples 1 to 10 and Comparative Examples 1 to 7

Used were adhesive base materials (styrene-isoprene-styrene block copolymer (SIS) and polyisobutylene (PIB)), a tackifier (alicyclic saturated hydrocarbon resin), a softener (liquid paraffin), a fentanyl citrate, an additional ingredient, absorption enhancers (propylene glycol fatty acid ester and diethyl sebacate), and antioxidants (dibutylhydroxytoluene (BHT), 2-mercaptobenzimidazole (2-MBI), butylhydroxyanisole (BHA), sodium metabisulfite, N-acetylcysteine, thioglycerol, sodium thioglycolate, ascorbic acid palmitate, ascorbic acid, soybean lecithin, and sodium edetate) specified in Tables 1 and 2 presented below. Each of adhesive solutions was obtained by measuring out the above ingredients so as to form a composition specified in Tables 1 and 2 presented below, and by mixing them in a solvent (ethyl acetate). Then, each of the adhesive solutions obtained was applied to a release liner (a PET film with a surface release-treated with silicone), and then the solvent was removed by drying to form an adhesive layer (the adhesive layer obtained has a thickness of 100 g/m$^2$). Subsequently, a backing (a PET film) was laminated on the adhesive layer, followed by cutting to obtain a patch. Thereafter, the obtained patch was sealed in a packaging bag made of an aluminum laminate film.

Here, the contents in Tables 1 and 2 are contents (% by mass) relative to the total mass of the adhesive layer, and the content of the adhesive base material is expressed in terms of solid content. A blank cell in Tables 1 and 2 indicates 0 (zero).

|  |  | Comp. Ex. 1 | Comp. Ex. 2 | Example 1 | Example 2 | Example 3 | Example 4 | Example 5 |
|---|---|---|---|---|---|---|---|---|
| Composition | Styrene-Isoprene-Styrene Block Copolymer (SIS) | 12.2 | 12.2 | 12.2 | 12.2 | 12.2 | 12.2 | 12.2 |
|  | Polyisobutylene (PIB) | 8.2 | 8.2 | 8.2 | 8.2 | 8.2 | 8.2 | 8.2 |
|  | Alicyclic Saturated Hydrocarbon Resin | 40.7 | 40.7 | 40.7 | 40.7 | 40.7 | 40.7 | 40.7 |
|  | Liquid Paraffin | 28.8 | 27.8 | 27.8 | 28.7 | 28.3 | 25.2 | 27.8 |
|  | Fentanyl Citrate | 4.0 | 4.0 | 4.0 | 4.0 | 4.0 | 4.0 | 4.0 |
|  | Other Ingredients | 3.1 | 3.1 | 3.1 | 3.1 | 3.1 | 3.1 | 3.1 |
|  | Propylene Glycol Fatty Acid Ester | 3.0 | 3.0 | 3.0 | 3.0 | 3.0 | 3.0 |  |
|  | Diethyl Sebacate |  |  |  |  |  |  | 3.0 |
|  | 2-Mercaptobenzimidazole (2-MBI) | 0.0 | 0.0 | 1.0 | 0.1 | 0.5 | 3.1 | 0.5 |
|  | Dibutylhydroxytoluene (BHT) | 0.0 | 1.0 | 0.0 | 0.0 | 0.0 | 0.5 | 0.5 |
|  | Total | 100.0 | 100.0 | 100.0 | 100.0 | 100.0 | 100.0 | 100.0 |
| Drug Temporal Stability Test | Degradaion Product A (RRT 0.4) | 0.10 | 0.01 | 0.01 | Undetectable | 0.01 | Undetectable | 0.01 |
|  | Degradaion Product B (RRT 1.4) | 0.50 | 0.29 | 0.01 | 0.04 | 0.03 | Undetectable | 0.03 |
| Skin Permeability Test | Skin Permeation Rate [μg/cm$^2$/hr] | — | 7.29 | 6.57 | 6.56 | 7.07 | 7.09 | — |

|  |  | Example 6 | Example 7 | Example 8 | Example 9 | Example 10 | Comp. Ex. 3 | Comp. Ex. 4 | Comp. Ex. 5 | Comp. Ex. 6 | Comp. Ex. 7 |
|---|---|---|---|---|---|---|---|---|---|---|---|
| Composition | Styrene-Isoprene-Styrene Block Copolymer (SIS) | 12.2 | 12.2 | 12.2 | 12.2 | 12.2 | 12.2 | 12.2 | 12.2 | 12.2 | 12.2 |
|  | Polyisobutylene (PIB) | 8.2 | 8.2 | 8.2 | 8.2 | 8.2 | 8.2 | 8.2 | 8.2 | 8.2 | 8.2 |
|  | Alicyclic Saturated Hydrocarbon Resin | 40.7 | 40.7 | 40.7 | 40.7 | 40.7 | 40.7 | 40.7 | 40.7 | 40.7 | 40.7 |
|  | Liquid Paraffin | 28.3 | 27.8 | 27.8 | 27.8 | 27.8 | 27.8 | 27.8 | 27.8 | 27.8 | 27.8 |
|  | Fentanyl Citrate | 4.0 | 4.0 | 4.0 | 4.0 | 4.0 | 4.0 | 4.0 | 4.0 | 4.0 | 4.0 |

-continued

|  |  | Example 6 | Example 7 | Example 8 | Example 9 | Example 10 | Comp. Ex. 3 | Comp. Ex. 4 | Comp. Ex. 5 | Comp. Ex. 6 | Comp. Ex. 7 |
|---|---|---|---|---|---|---|---|---|---|---|---|
|  | Other Ingredients | 3.1 | 3.1 | 3.1 | 3.1 | 3.1 | 3.1 | 3.1 | 3.1 | 3.1 | 3.1 |
|  | Propylene Glycol Fatty Acid Ester | 3.0 | 3.0 | 3.0 | 3.0 | 3.0 | 3.0 | 3.0 | 3.0 | 3.0 | 3.0 |
|  | Sodium Metabisulfite | 0.5 | 0.5 |  |  |  |  |  |  |  |  |
|  | N-Acetylcysteine |  |  | 0.5 |  |  |  |  |  |  |  |
|  | Thioglycerol |  |  |  | 0.5 |  |  |  |  |  |  |
|  | Sodium Thioglycolate |  |  |  |  | 0.5 |  |  |  |  |  |
|  | Ascorbic Acid Palmitate |  |  |  |  |  | 0.5 |  |  |  |  |
|  | Ascorbic Acid |  |  |  |  |  |  | 0.5 |  |  |  |
|  | Soybean Lecithin |  |  |  |  |  |  |  | 0.5 |  |  |
|  | Sodium Edetate |  |  |  |  |  |  |  |  | 0.5 |  |
|  | Dibutyl-hydroxy-toluene (BHT) | 0.0 | 0.5 | 0.5 | 0.5 | 0.5 | 0.5 | 0.5 | 0.5 | 0.5 | 0.5 |
|  | Butylhydroxy-anisole (BHA) |  |  |  |  |  |  |  |  |  | 0.5 |
|  | Total | 100.0 | 100.0 | 100.0 | 100.0 | 100.0 | 100.0 | 100.0 | 100.0 | 100.0 | 100.0 |
| Drug Temporal Stability Test | Degradaion Product A (RRT 0.4) | 0.03 | 0.02 | 0.02 | 0.01 | 0.01 | 0.02 | 0.01 | Undetectable | Undetectable | Undetectable |
|  | Degradaion Product B (RRT 1.4) | 0.04 | 0.03 | 0.09 | 0.08 | 0.08 | 0.18 | 0.16 | 0.59 | 0.47 | 0.38 |

Using each of the patches obtained, a "drug temporal stability test" was conducted in the method described below. In addition, using each of the patches obtained in Examples 1 to 4 and Comparative Example 2, a "skin permeability test" was conducted in the method described below. The obtained results are presented in in Tables 1 and 2.

<Drug Temporal Stability Test>

The packaging bag of each of the sealed patches immediately after the production was opened to take out the patch, the release liner was removed, and thereafter the patch was folded in half with the two sides of the adhesive layer stuck together inside. This was immersed in 1 mL of tetrahydrofuran for liquid chromatography precisely measured out beforehand, followed by shaking for 30 minutes for extraction. Then, methanol was added so that the resultant solution had exactly 10 mL, followed by mixing. The obtained solution was filtered through a membrane filter having a pore size of 0.5 μm or less to prepare a sample solution. Subsequently, peak areas of the fentanyl and analogs (degradation products) in the sample solution were determined by high performance liquid chromatography, and the amount of each of the analogs was calculated in accordance with the following formula:

Amount (% by mass) of each analog=$A_{T0}/(A_F+A_T) \times 100$ (where $A_{T0}$ denotes the peak area of the concerned analog, $A_F$ denotes the peak area of the fentanyl, and $A_T$ denotes the sum total of the peak areas of all the analogs). The results are presented in Tables 1 and 2.

Here, RRT denotes a ratio of the retention time of each analog relative to the retention time of fentanyl, which is set to 1, RRT 0.4 presents the amount (% by mass) of a dephenethylated fragment of the fentanyl or its analog, and RRT 1.4 presents the amount (% by mass) of fentanyl N-oxide.

As is apparent from the results presented in Tables 1 and 2, the patches of the present invention (Examples 1 to 10), in each of which the adhesive layer contained, as an antioxidant, it was observed that an antioxidant having a sulfur atom in its molecule, were very good in the temporal stability of the drug because the generation of the drug degradation products was notably inhibited.

<Skin Permeability Test>

Each patch sealed in the packaging bag was taken out with the packaging bag opened, and the skin permeability of the patch was evaluated by a skin permeability test in vitro using hairless mouse skin explained below.

Specifically, after the dorsal skin of a 6 to 9 week-old hairless mouse was removed, the fat on the dermis side was carefully removed, and the resultant skin was attached to a flow through cell (3 cm$^2$) such that the dermis side was arranged on a receptor layer with water at 37° C. circulated around the outer periphery of the receptor layer. Each patch was applied to the stratum corneum side of this skin, physiological saline was used as the receptor layer, and sampling was performed every hour over 24 hours at a rate of 5 ml/hour. Thereafter, the flow volume per hour was accurately measured, the drug concentration was measured by high performance liquid chromatography, and the drug permeation rate in a steady state was determined by calculating the permeation rate per hour in accordance with the following formula:

Drug permeation rate [μg/cm$^2$/hr]=(drug concentration [μg/ml]×flow volume [ml])/preparation-applied area [cm$^2$].

The results are presented in Table 1.

As is apparent from the results presented in Table 1, the patches of the present invention (Examples 1 to 4) in which the adhesive layer contains, as the antioxidant, the antioxidant having a sulfur atom in its molecule were observed demonstrating that the transdermal absorbability of the drug which is the basic performance of the patch did not decrease but was kept at a high level.

INDUSTRIAL APPLICABILITY

As has been explained above, according to the present invention, a patch containing, as a drug, at least one selected from the group consisting of fentanyl and salts thereof can be made capable of more reliably preventing the drug from degrading over time without deteriorating the basic performance such as the transdermal absorbability of the drug, so that it is possible to provide a clinically useful transdermal administration patch that is notably superior to a conventional patch in terms of the temporal stability of the drug.

Hence, use of the transdermal administration patch containing at least one selected from the group consisting of fentanyl and salts thereof according to the present invention makes it possible to deliver the fentanyl and the salts thereof into the body stably over a long period of time, and thereby to use the pharmacological effect of the fentanyl and the salts thereof effectively in a stable and persistent manner.

Therefore, the transdermal administration patch containing at least one selected from the group consisting of fentanyl and salts thereof according to the present invention can be very powerful means for pain relief for patients and others who have difficulty in injection or oral administration of narcotic analgesic agents.

The invention claimed is:

1. A patch comprising a backing, and an adhesive layer laminated on at least one surface of the backing, wherein
the adhesive layer contains at least one selected from the group consisting of fentanyl and salts thereof, and contains an adhesive base material and an antioxidant having a sulfur atom in its molecule,
said antioxidant being at least one selected from the group consisting of 2-mercaptobenzimidazole and sodium metabisulfite.

2. The patch according to claim 1, wherein the adhesive base material is a rubber-based adhesive base material.

3. The patch according to claim 1, wherein
a content of the fentanyl and the salts thereof is 0.05 to 20% by mass relative to a total mass of the adhesive layer,
a content of the adhesive base material is 0.1 to 98% by mass relative to the total mass of the adhesive layer in terms of solid content, and
a content of the antioxidant having a sulfur atom in its molecule is 0.01 to 5% by mass relative to the total mass of the adhesive layer.

4. The patch according to claim 1, wherein the adhesive layer further contains a fatty acid ester as an absorption enhancer.

5. The patch according to claim 4, wherein a content of the absorption enhancer is 0.01 to 20% by mass relative to the total mass of the adhesive layer.

6. The patch according to claim 1, wherein the adhesive layer further contains a phenolic antioxidant.

7. The patch according to claim 6, wherein a content of the phenolic antioxidant is 0.01 to 5% by mass relative to the total mass of the adhesive layer.

8. The patch according to claim 1, wherein
the adhesive layer further contains, as a desalting agent, at least one selected from the group consisting of basic alkaline metal salts, alkaline earth metal salts, alkali metal hydroxides, alkali earth metal hydroxides and low-molecular weight compounds containing basic nitrogen, and
a content of the desalting agent is 0.01 to 15% by mass relative to the total mass of the adhesive layer.

9. The patch according to claim 1, wherein
the adhesive layer further contains, as a tackifier, at least one selected from the group consisting of alicyclic saturated hydrocarbon resins, terpene resins, rosin resins, rosin ester resins, and oil-soluble phenolic resins, and
a content of the tackifier is 0.1 to 70% by mass relative to the total mass of the adhesive layer.

10. The patch according to claim 1, wherein
the adhesive layer further contains, as a softener, at least one selected from the group consisting of liquid paraffin, squalane, olive oil, camellia oil, persic oil, and arachis oil, and
a content of the softener is 1 to 70% by mass relative to the total mass of the adhesive layer.

* * * * *